(12) United States Patent
Pronina

(10) Patent No.: US 11,904,909 B2
(45) Date of Patent: Feb. 20, 2024

(54) ENABLING RIDE SHARING DURING PANDEMICS

(71) Applicant: GM Cruise Holdings LLC, San Francisco, CA (US)

(72) Inventor: Olga Pronina, Danville, CA (US)

(73) Assignee: GM Cruise Holdings LLC, San Francisco, CA (US)

(*) Notice: Subject to any disclaimer, the term of this patent is extended or adjusted under 35 U.S.C. 154(b) by 218 days.

(21) Appl. No.: 17/358,769

(22) Filed: Jun. 25, 2021

(65) Prior Publication Data

US 2022/0410930 A1    Dec. 29, 2022

(51) Int. Cl.
| | |
|---|---|
| *B60W 60/00* | (2020.01) |
| *H04W 4/44* | (2018.01) |
| *H04W 4/48* | (2018.01) |
| *A61B 5/01* | (2006.01) |
| *A61B 7/00* | (2006.01) |
| *A61B 5/00* | (2006.01) |

(52) U.S. Cl.
CPC .............. *B60W 60/007* (2020.02); *A61B 5/01* (2013.01); *A61B 5/6893* (2013.01); *A61B 7/003* (2013.01); *H04W 4/44* (2018.02); *H04W 4/48* (2018.02); *B60W 2540/221* (2020.02); *B60W 2556/45* (2020.02)

(58) Field of Classification Search
CPC ......... B60W 60/007; B60W 2540/221; B60W 2556/45; A61B 5/01; A61B 5/6893; A61B 7/003; A61B 5/024; A61B 5/0816; A61B 5/113; A61B 2562/0219; A61B 5/0022; A61B 5/08; A61B 5/7267; A61B 5/015; A61B 5/0823; H04W 4/44; H04W 4/48; G16H 50/20
See application file for complete search history.

(56) References Cited

U.S. PATENT DOCUMENTS

| | | | | |
|---|---|---|---|---|
| 9,159,021 | B2* | 10/2015 | Hawkins | G06N 20/00 |
| 9,836,057 | B2* | 12/2017 | Fairfield | G08G 1/202 |
| 10,318,878 | B2* | 6/2019 | Hawkins | G06N 7/01 |
| 11,104,347 | B1* | 8/2021 | Morizumi | G16H 50/20 |
| 11,318,960 | B1* | 5/2022 | McKnew | B60S 1/64 |
| 11,370,391 | B1* | 6/2022 | Gammelgard | B60R 25/1004 |
| 2012/0071777 | A1* | 3/2012 | MacAuslan | A61B 5/7282 |
| | | | | 600/529 |

(Continued)

FOREIGN PATENT DOCUMENTS

| | | | |
|---|---|---|---|
| CN | 110289089 A | * 9/2019 | |
| JP | 2017206239 A | * 11/2017 | ............ B60W 30/06 |

(Continued)

*Primary Examiner* — Peter D Nolan
*Assistant Examiner* — Peter Y Ning
(74) *Attorney, Agent, or Firm* — Novak Druce Carroll LLP

(57) ABSTRACT

The disclosed technology provides solutions for protecting the health of ride-sharing passengers by detecting passenger illnesses, and taking precautions to safely address potentially exposed vehicles. A process of the disclosed technology can include steps for: collecting sensor-data corresponding with one or more AV passengers, determining a likelihood that at least one of the AV passengers is suffering from a physical illness, and transmitting a wellness notification to a fleet management system if the likelihood exceeds a predetermined threshold. Systems and machine-readable media are also provided.

20 Claims, 5 Drawing Sheets

(56) References Cited

U.S. PATENT DOCUMENTS

| | | | |
|---|---|---|---|
| 2012/0283598 A1* | 11/2012 | Horii | A61B 5/0816 |
| | | | 600/586 |
| 2018/0201226 A1* | 7/2018 | Falkson | B60R 25/257 |
| 2019/0225232 A1* | 7/2019 | Blau | G05D 1/0088 |
| 2019/0391581 A1* | 12/2019 | Vardaro | A61B 5/02055 |
| 2021/0399911 A1* | 12/2021 | Jorasch | H04L 12/1822 |
| 2022/0032956 A1* | 2/2022 | Wolff | B60W 50/085 |
| 2022/0292134 A1* | 9/2022 | Shahbazi Mirzahasanloo | |
| | | | H04W 12/33 |
| 2022/0378302 A1* | 12/2022 | Marcolino Quintao | |
| | | Severgnini | A61B 5/0006 |
| 2023/0087363 A1* | 3/2023 | Pardasani | G16H 50/30 |
| | | | 382/128 |
| 2023/0259864 A1* | 8/2023 | Decrop | A61B 5/0022 |
| | | | 705/7.41 |

FOREIGN PATENT DOCUMENTS

| | | | | |
|---|---|---|---|---|
| JP | 2022062701 A | * | 4/2022 | A61B 5/0022 |
| WO | WO-2022258302 A1 | * | 12/2022 | |

\* cited by examiner

ENABLING RIDE SHARING DURING PANDEMICS

BACKGROUND

1. Technical Field

The disclosed technology provides solutions for reducing the transmission of infectious diseases and in particular, reducing exposure risks for passengers of a ride-sharing service.

2. Introduction

Autonomous vehicles (AVs) are vehicles having computers and control systems that perform driving and navigation tasks that are conventionally performed by a human driver. As AV technologies continue to advance, they will be increasingly used to improve transportation efficiency and safety. As such, AVs will need to perform many of the functions that are conventionally performed by human drivers, such as performing navigation and routing tasks necessary to provide a safe and efficient transportation. Such tasks may require the collection and processing of large quantities of data using various sensor types, including but not limited to cameras and/or Light Detection and Ranging (LiDAR) sensors disposed on the AV.

BRIEF DESCRIPTION OF THE DRAWINGS

Certain features of the subject technology are set forth in the appended claims. However, the accompanying drawings, which are included to provide further understanding, illustrate disclosed aspects and together with the description serve to explain the principles of the subject technology. In the drawings:

DETAILED DESCRIPTION

Figure 1:
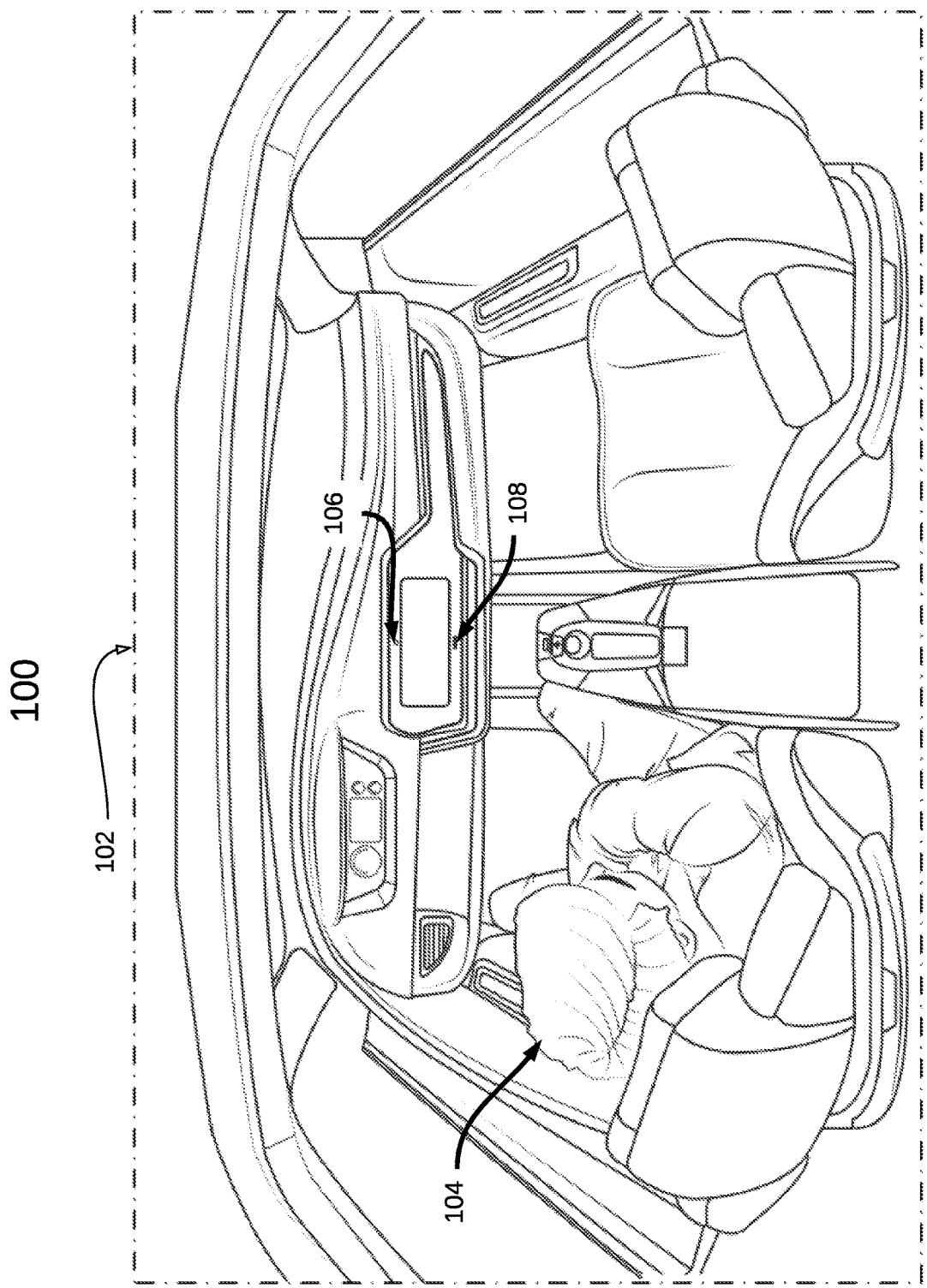
FIG. 1 conceptually illustrates an example of an autonomous vehicle (AV) cabin in which sensor-data can be collected, according to some aspects of the disclosed technology.

The detailed description set forth below is intended as a description of various configurations of the subject technology and is not intended to represent the only configurations in which the subject technology can be practiced. The appended drawings are incorporated herein and constitute a part of the detailed description. The detailed description includes specific details for the purpose of providing a more thorough understanding of the subject technology. However, it will be clear and apparent that the subject technology is not limited to the specific details set forth herein and may be practiced without these details. In some instances, structures and components are shown in block diagram form in order to avoid obscuring the concepts of the subject technology.

As described herein, one aspect of the present technology is the gathering and use of data available from various sources to improve quality and experience. The present disclosure contemplates that in some instances, this gathered data may include personal information. The present disclosure contemplates that the entities involved with such personal information respect and value privacy policies and practices.

Especially in large metropolitan areas, ride-sharing services have become a popular means of transportation. In common deployment, fleet vehicles, such as autonomous vehicles (AVs), can be dispatched to pick-up passengers at a specified location (e.g., a user specified pick-up location), and transport them to an eventual, final, drop-off location. Once the ride service is completed, the AV then becomes available to new/subsequent passengers. In some ride-sharing deployments, dispatch and scheduling operations are facilitated using one or more remote systems (e.g., a fleet management system), for example, that can be tasked with managing AV dispatch to various users (passengers) across different map locations. For example, AV dispatch may be performed in such a manner that vehicle dispatch is performed based on a distance between an operating fleet vehicle and the requesting rider/passenger.

However, one concern for public transportation generally, and ride-sharing services in particular, is the exposure of different passengers to one-another, and/or to contaminated areas for example, where social-distancing is desired due to infectious disease transmission concerns, such as in times of active pandemics. By way of example, due to health concerns, a passenger may not want to occupy a space (e.g., a vehicle cabin) that was recently occupied by someone exhibiting signs of illness, such as a fever or respiratory irregularities, such as coughing and/or sneezing, etc.

Aspects of the disclosed technology address the foregoing concerns by providing solutions for detecting possible user (passenger) illness states, and making changes to the manner in which fleet AVs are deployed, e.g., to limit passenger exposure risk. In some aspects, the detections of potential illness states in one or more passengers may cause changes to normal vehicle dispatch protocols. In some aspects, AVs that have been exposed to potentially ill passengers may be temporarily suspended from normal operation, for example by being recalled to a depot for cleaning, or by being commissioned to perform certain automatic cleaning procedures. By detecting and proactively limiting opportunities for disease transmission, aspects of the disclosed technology improve passenger and safety while also furthering the public's interest in mitigating disease transmission risks.

FIG. 1 conceptually illustrates an example of an autonomous vehicle (AV) cabin 100 in which sensor-data can be collected, e.g., for various passengers, and used to determine a likelihood that at least one of the AV passengers is suffering from a physical illness. In the illustrated example, AV cabin 100 includes various sensors that include one or more cameras 106, one or more microphones 108, and/or one or more thermometers 110. It is understood that additional (or fewer) sensors of different types may be implemented, without departing from the scope of the disclosed technology. By way of example, accelerometers (not illustrated) may be disposed in various portions of the AV cabin 100, such as in passenger seats and/or seatbelts to detect bodily movements (e.g., heartbeat and/or breath rate), for one or more passengers in the AV cabin 100.

In some implementations, cameras 106 may include a thermal camera (or other thermal sensing device) that is configured to detect a temperature of various objects, for example, within the cabin 100. In such approaches, the camera 106 may be used to determine (or estimate) a temperature of one or more of occupants of cabin 100, such as one or more passengers 104. By way of example, sensor-data collected from camera 106 may include thermal imaging that can be used to determine a likelihood that one or more of the passengers 104 has a fever, and is therefore likely to be afflicted with a physical illness, such as infection by a transmissible disease.

In a similar manner, microphone 108 may be used to detect sounds emitted by passengers 104 that can be used to infer whether or not one or more of the passengers 104 may be exhibiting respiratory irregularities, and therefore likely to be suffering from a physical illness, such as a transmissible disease. By way of example, microphone 108 may be used to detect respiratory anomalies, such as coughing, sneezing, and/or labored breathing from passengers 104. The collected sensor data can be used to determine a likelihood that one or more of the passengers 104 are ill. In some aspects, determinations regarding the likelihood of passenger illness can be made locally, e.g., at a computing system of the AV. For example, one or more notifications (e.g., a wellness notification) may be transmitted by the AV, to the fleet management system, if the likelihood exceeds a predetermined threshold. The wellness notification can include details about the health status of the one or more passengers 104. In such approaches, the fleet management system can be configured to remove vehicles from operation if it is determined that they are likely to have been occupied by a sick passenger. As such, the contaminated AV can be cleaned, or otherwise subject to other contamination protocols before being returned to operation.

In other implementations, determinations regarding passenger health may be made at one or more remote systems, for example, that are configured to receive the sensor-data collected at the AV, and to determine a likelihood that one or more of the passengers are suffering from a physical illness. Further details regarding communications between an AV and a fleet management system are provided with respect to FIG. 2.

Figure 2:
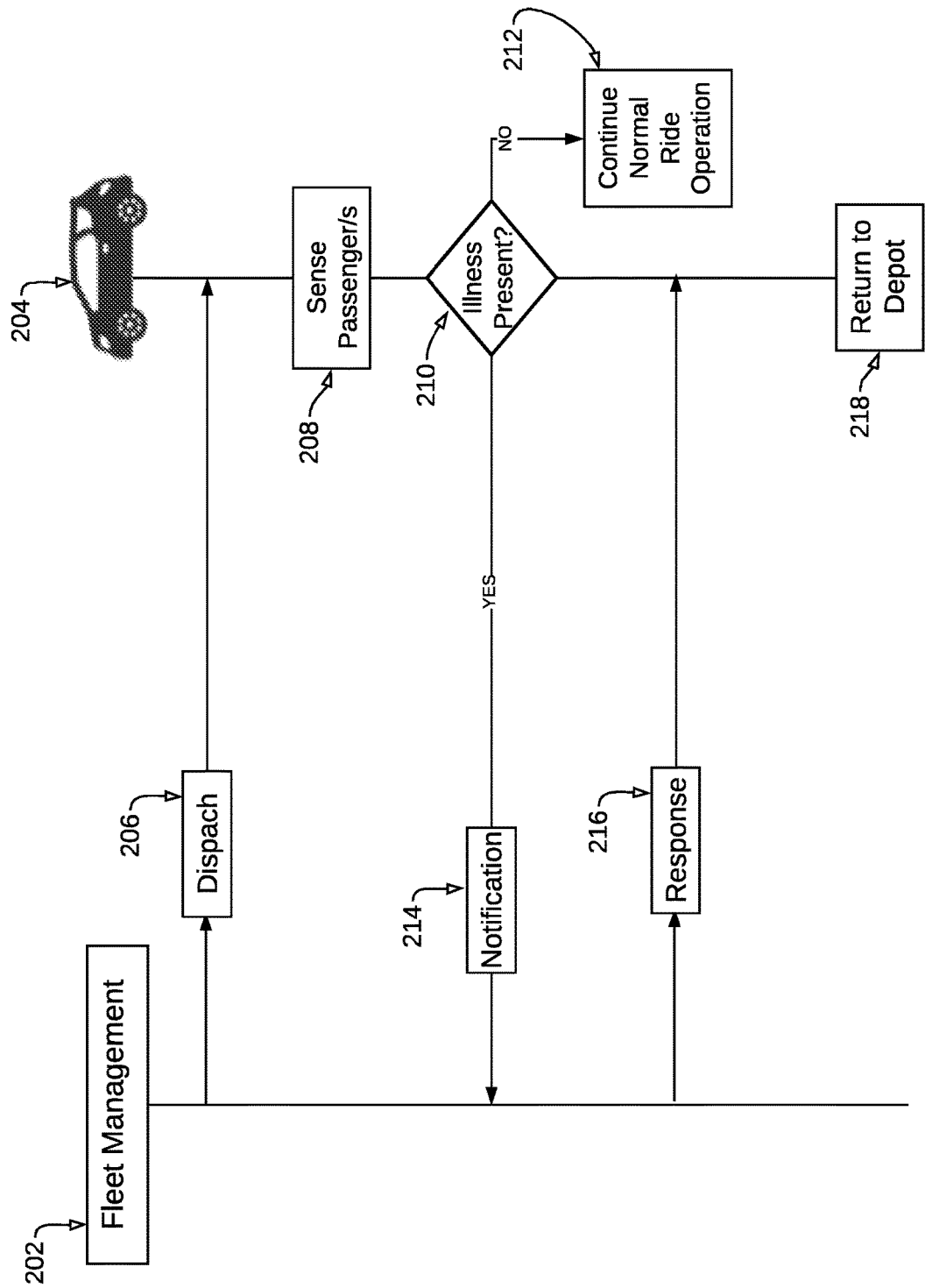
FIG. 2 illustrates a conceptual diagram of communications between a fleet management system and an AV, according to some aspects of the disclosed technology.

In particular, FIG. 2 illustrates a conceptual diagram of communications 200 between a fleet management system 202 and an AV 204, according to some aspects of the disclosed technology. In the example of FIG. 2, the fleet management system can issue a vehicle dispatch notification 206 to an AV 204, for example, to dispatch AV 204 in order to provide a ride service to a passenger (rider). Upon arrival at the passenger's pick-up location, sensor-data can be collected by the AV 204 for one or more passengers serviced by the pick-up (208). In some implementations, sensor-data may be collected for the passenger/s before the passenger/s enter the AV cabin. By way of example, one or more outward facing (or exterior) sensors (e.g., thermal cameras, and/or microphones) may collect sensor-data for one or more passengers as they approach the AV.

In other implementations, sensor-data can be collected once the passenger/s have entered the AV cabin. As discussed above, sensor-data that is collected in the AV cabin can be collected by one or more inward facing cameras, microphones, thermal sensors, and/or accelerometers, etc. The collected sensor data can then be used to determine if any of the passengers are exhibiting signs of physical illness, e.g., fever, coughing, and/or sneezing, etc. In some aspects, a likelihood of illness may be determined/computed based on the collected sensor data (210). By way of example, sensor data may be provided to a machine-learning model that is configured to make predictions regarding passenger health states. In other implementations, passenger health states may be inferred directly from the collected data; for example, if sensor data indicates that one or more of the passengers has a fever, then the affected passenger may be automatically identified having a potential illness.

If the likelihood of passenger illness is low, e.g., it is determined that there are no health-compromised passengers, then the AV can continue normal operation (212). Alternatively, if it is determined that one or more of the passengers is likely to be suffering from a physical health abnormality, then a notification (e.g., a wellness notification) 214 can be provided from the AV 204 back to the fleet management system 202.

In some examples, based on the wellness notification, the fleet management system 202 can determine an appropriate course of action for the AV 204. By way of example, it may be determined that the AV 204 should be temporarily removed from operation, e.g., to avoid contact between the potentially infected AV cabin and additional passengers. In other implementations, it may be determined that certain on-board cleaning procedures should be initiated. For example, the AV 204 may be equipped with self-cleaning capabilities, and may be capable of disinfecting any areas, such as the interior cabin, that could pose a health concern for subsequent passengers.

Determinations as to how AV 204 should respond given contact with an ill (or likely ill) passenger, can be communicated to the AV 204, by the fleet management system 202, via a response 216. As mentioned above, in some aspects, the AV 204 may be temporarily suspended from service, e.g., to undergo cleaning/disinfecting. By way of example, response 216 may contain information/instructions that are configured to cause the AV 204 to return to a depot for cleaning (218).

Figure 3:
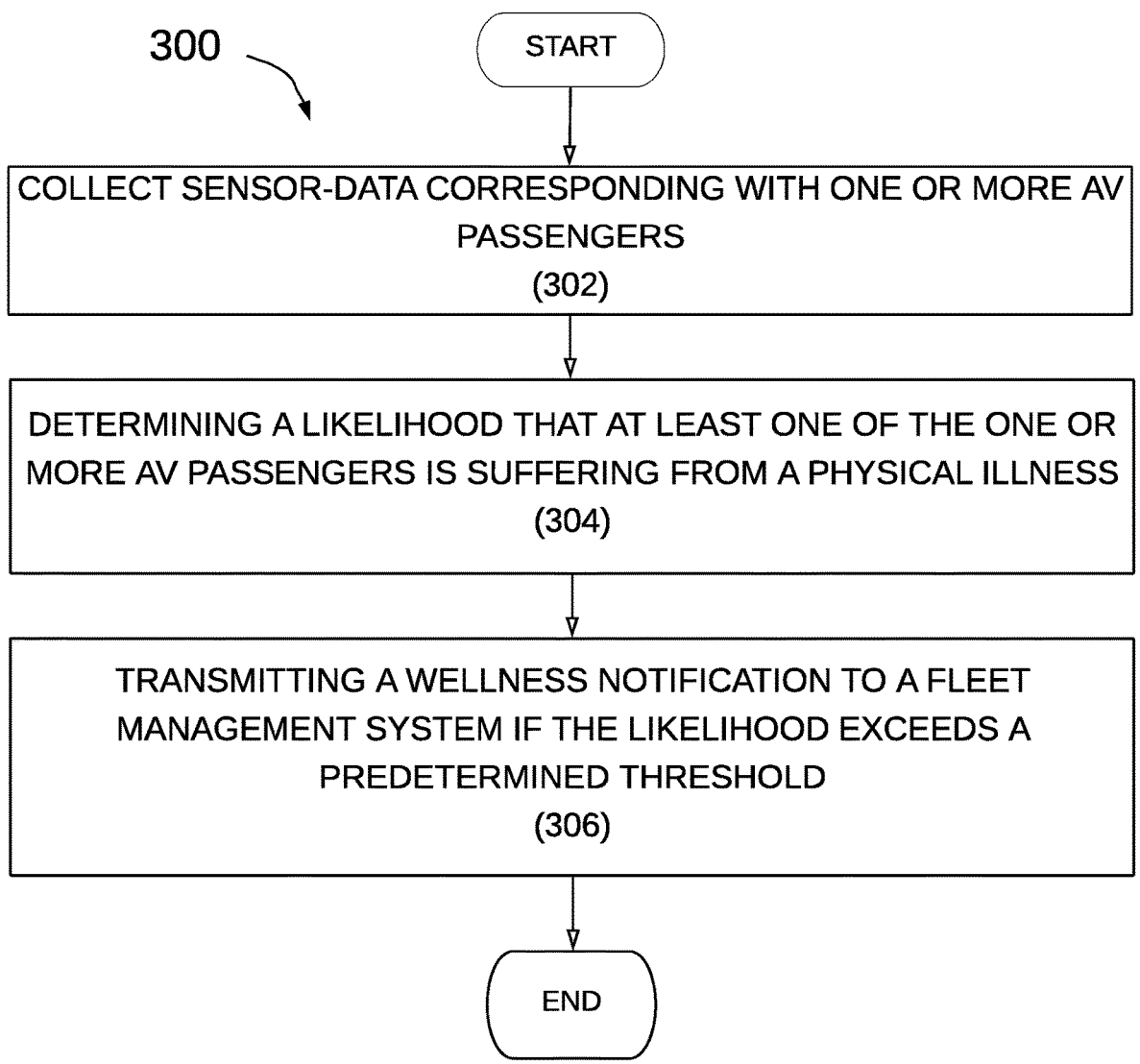
FIG. 3 illustrates a block diagram of a process for assessing a passenger health state, according to some aspects of the disclosed technology.

FIG. 3 illustrates a block diagram of a process 300 for assessing a passenger health state, according to some aspects of the disclosed technology. Process 300 begins with step 302 in which sensor-data is collected (e.g., by an AV), and wherein the sensor-data is associated with at least one AV passenger. By way of example, the sensor data may include data collected using a camera or other thermal imaging device (e.g., a thermal camera), one or more microphones, and/or one or more thermometers. Depending on the desired implementation, the sensor data may be collected from the passenger/s either inside the AV (e.g., inside the AV cabin), or outside the AV, for example, before the passenger enters the AV cabin.

In step 304, the process 300 includes determining a likelihood that at least one of the AV passengers is suffering from a physical illness, e.g., based on the collected sensor data. Depending on the desired implementation, determinations of illness likelihood can be made locally (e.g., at the AV), or may be made using on or more remote systems. For implementations in which illness likelihoods are determined locally, such determinations may be transmitted (e.g., as wellness notifications) to one or more remote systems (step 306), such as a fleet management system, as discussed above with respect to FIG. 2.

Alternatively, in implementations where illness determinations (or likelihood determinations) are made by a remote system, the collected-sensor data may be transmitted to the remote system (e.g., fleet management system), and used to make the determination.

Figure 4:
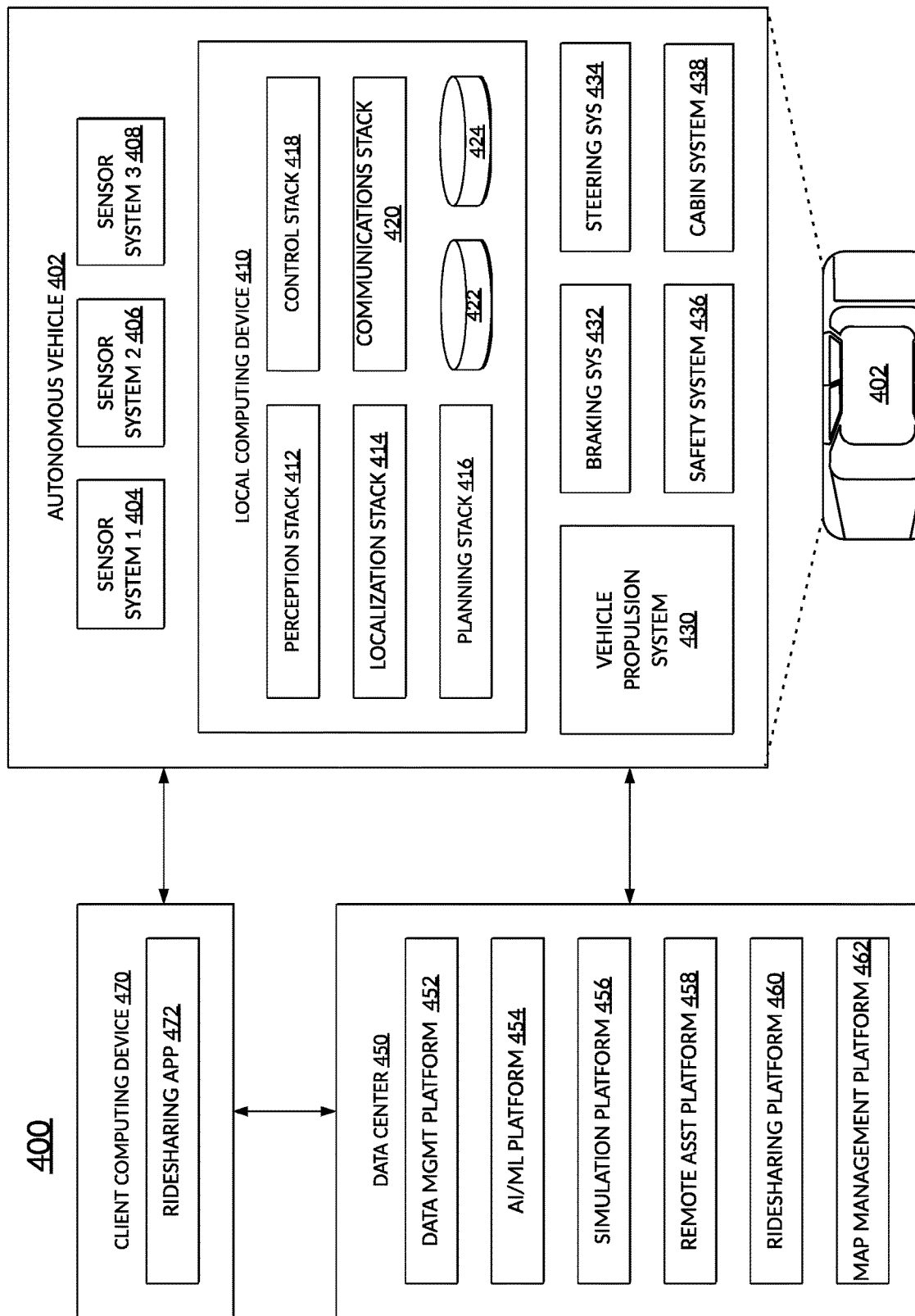
FIG. 4 illustrates an example system environment that can be used to facilitate AV dispatch and operations, according to some aspects of the disclosed technology.

Turning now to FIG. 4 illustrates an example of an AV management system 500. One of ordinary skill in the art will understand that, for the AV management system 400 and any system discussed in the present disclosure, there can be additional or fewer components in similar or alternative configurations. The illustrations and examples provided in the present disclosure are for conciseness and clarity. Other embodiments may include different numbers and/or types of elements, but one of ordinary skill the art will appreciate that such variations do not depart from the scope of the present disclosure.

In this example, the AV management system 400 includes an AV 402, a data center 450, and a client computing device 470. The AV 402, the data center 450, and the client computing device 470 can communicate with one another over one or more networks (not shown), such as a public network (e.g., the Internet, an Infrastructure as a Service (IaaS) network, a Platform as a Service (PaaS) network, a Software as a Service (SaaS) network, other Cloud Service Provider (CSP) network, etc.), a private network (e.g., a Local Area Network (LAN), a private cloud, a Virtual Private Network (VPN), etc.), and/or a hybrid network (e.g., a multi-cloud or hybrid cloud network, etc.).

AV 402 can navigate about roadways without a human driver based on sensor signals generated by multiple sensor systems 404, 406, and 408. The sensor systems 404-408 can include different types of sensors and can be arranged about the AV 402. For instance, the sensor systems 404-408 can comprise Inertial Measurement Units (IMUs), cameras (e.g., still image cameras, video cameras, etc.), light sensors (e.g., LIDAR systems, ambient light sensors, infrared sensors, etc.), RADAR systems, GPS receivers, audio sensors (e.g., microphones, Sound Navigation and Ranging (SONAR) systems, ultrasonic sensors, etc.), engine sensors, speedometers, tachometers, odometers, altimeters, tilt sensors, impact sensors, airbag sensors, seat occupancy sensors, open/closed door sensors, tire pressure sensors, rain sensors, and so forth. For example, the sensor system 404 can be a camera system, the sensor system 406 can be a LIDAR system, and the sensor system 408 can be a RADAR system. Other embodiments may include any other number and type of sensors.

AV 402 can also include several mechanical systems that can be used to maneuver or operate AV 402. For instance, the mechanical systems can include vehicle propulsion system 430, braking system 432, steering system 434, safety system 436, and cabin system 438, among other systems. Vehicle propulsion system 430 can include an electric motor, an internal combustion engine, or both. The braking system 432 can include an engine brake, brake pads, actuators, and/or any other suitable componentry configured to assist in decelerating AV 402. The steering system 434 can include suitable componentry configured to control the direction of movement of the AV 402 during navigation. Safety system 436 can include lights and signal indicators, a parking brake, airbags, and so forth. The cabin system 438 can include cabin temperature control systems, in-cabin entertainment systems, and so forth. In some embodiments, the AV 402 may not include human driver actuators (e.g., steering wheel, handbrake, foot brake pedal, foot accelerator pedal, turn signal lever, window wipers, etc.) for controlling the AV 402. Instead, the cabin system 438 can include one or more client interfaces (e.g., Graphical User Interfaces (GUIs), Voice User Interfaces (VUIs), etc.) for controlling certain aspects of the mechanical systems 430-438.

AV 402 can additionally include a local computing device 410 that is in communication with the sensor systems 404-408, the mechanical systems 430-438, the data center 450, and the client computing device 470, among other systems. The local computing device 410 can include one or more processors and memory, including instructions that can be executed by the one or more processors. The instructions can make up one or more software stacks or components responsible for controlling the AV 402; communicating with the data center 450, the client computing device 470, and other systems; receiving inputs from riders, passengers, and other entities within the AV's environment; logging metrics collected by the sensor systems 404-408; and so forth. In this example, the local computing device 410 includes a perception stack 412, a mapping and localization stack 414, a planning stack 416, a control stack 418, a communications stack 420, an HD geospatial database 422, and an AV operational database 424, among other stacks and systems.

Perception stack 412 can enable the AV 402 to "see" (e.g., via cameras, LIDAR sensors, infrared sensors, etc.), "hear" (e.g., via microphones, ultrasonic sensors, RADAR, etc.), and "feel" (e.g., pressure sensors, force sensors, impact sensors, etc.) its environment using information from the sensor systems 404-408, the mapping and localization stack 414, the HD geospatial database 422, other components of the AV, and other data sources (e.g., the data center 450, the client computing device 470, third-party data sources, etc.). The perception stack 412 can detect and classify objects and determine their current and predicted locations, speeds, directions, and the like. In addition, the perception stack 412 can determine the free space around the AV 402 (e.g., to maintain a safe distance from other objects, change lanes, park the AV, etc.). The perception stack 412 can also identify environmental uncertainties, such as where to look for moving objects, flag areas that may be obscured or blocked from view, and so forth.

Mapping and localization stack 414 can determine the AV's position and orientation (pose) using different methods from multiple systems (e.g., GPS, IMUs, cameras, LIDAR, RADAR, ultrasonic sensors, the HD geospatial database 422, etc.). For example, in some embodiments, the AV 402 can compare sensor data captured in real-time by the sensor systems 404-408 to data in the HD geospatial database 422 to determine its precise (e.g., accurate to the order of a few centimeters or less) position and orientation. The AV 402 can focus its search based on sensor data from one or more first sensor systems (e.g., GPS) by matching sensor data from one or more second sensor systems (e.g., LIDAR). If the mapping and localization information from one system is unavailable, the AV 402 can use mapping and localization information from a redundant system and/or from remote data sources.

The planning stack 416 can determine how to maneuver or operate the AV 402 safely and efficiently in its environment. For example, the planning stack 416 can include an AV routing system that is configured to identify and select navigation routes. By way of example, the planning stack 416 can receive the location, speed, and direction of the AV 402, geospatial data, data regarding objects sharing the road with the AV 402 (e.g., pedestrians, bicycles, vehicles, ambulances, buses, cable cars, trains, traffic lights, lanes, road markings, etc.) or certain events occurring during a trip (e.g., emergency vehicle blaring a siren, intersections, occluded areas, street closures for construction or street repairs, double-parked cars, etc.), traffic rules and other safety standards or practices for the road, user input, and other relevant data for directing the AV 402 from one point to another. The planning stack 416 can determine multiple sets of one or more mechanical operations that the AV 402 can perform (e.g., go straight at a specified rate of acceleration, including maintaining the same speed or decelerating; turn on the left blinker, decelerate if the AV is above a threshold range for turning, and turn left; turn on the right blinker, accelerate if the AV is stopped or below the threshold range for turning, and turn right; decelerate until completely stopped and reverse; etc.), and select the best one to meet changing road conditions and events. If something unexpected happens, the planning stack 416 can select from multiple backup plans to carry out. For example, while preparing to change lanes to turn right at an intersection, another vehicle may aggressively cut into the destination lane, making the lane change unsafe. The planning stack 416 could have already determined an alternative plan for such an event, and upon its occurrence, help to direct the AV 402 to go around the block instead of blocking a current lane while waiting for an opening to change lanes.

The control stack 418 can manage the operation of the vehicle propulsion system 430, the braking system 432, the steering system 434, the safety system 436, and the cabin system 438. The control stack 418 can receive sensor signals from the sensor systems 404-408 as well as communicate with other stacks or components of the local computing device 410 or a remote system (e.g., the data center 450) to effectuate operation of the AV 402. For example, the control stack 418 can implement the final path or actions from the multiple paths or actions provided by the planning stack 416. This can involve turning the routes and decisions from the planning stack 416 into commands for the actuators that control the AV's steering, throttle, brake, and drive unit.

The communication stack 420 can transmit and receive signals between the various stacks and other components of the AV 402 and between the AV 402, the data center 450, the client computing device 470, and other remote systems. The communication stack 420 can enable the local computing device 410 to exchange information remotely over a network, such as through an antenna array or interface that can provide a metropolitan WIFI network connection, a mobile or cellular network connection (e.g., Third Generation (3G), Fourth Generation (4G), Long-Term Evolution (LTE), 5th Generation (5G), etc.), and/or other wireless network connection (e.g., License Assisted Access (LAA), Citizens Broadband Radio Service (CBRS), MULTEFIRE, etc.). The communication stack 420 can also facilitate local exchange of information, such as through a wired connection (e.g., a user's mobile computing device docked in an in-car docking station or connected via Universal Serial Bus (USB), etc.) or a local wireless connection (e.g., Wireless Local Area Network (WLAN), Bluetooth®, infrared, etc.).

The HD geospatial database 422 can store HD maps and related data of the streets upon which the AV 402 travels. In some embodiments, the HD maps and related data can comprise multiple layers, such as an areas layer, a lanes and boundaries layer, an intersections layer, a traffic controls layer, and so forth. The areas layer can include geospatial information indicating geographic areas that are drivable (e.g., roads, parking areas, shoulders, etc.) or not drivable (e.g., medians, sidewalks, buildings, etc.), drivable areas that constitute links or connections (e.g., drivable areas that form the same road) versus intersections (e.g., drivable areas where two or more roads intersect), and so on. The lanes and boundaries layer can include geospatial information of road lanes (e.g., lane centerline, lane boundaries, type of lane boundaries, etc.) and related attributes (e.g., direction of travel, speed limit, lane type, etc.). The lanes and boundaries layer can also include 3D attributes related to lanes (e.g., slope, elevation, curvature, etc.). The intersections layer can include geospatial information of intersections (e.g., crosswalks, stop lines, turning lane centerlines and/or boundaries, etc.) and related attributes (e.g., permissive, protected/permissive, or protected only left turn lanes; legal or illegal U-turn lanes; permissive or protected only right turn lanes; etc.). The traffic controls lane can include geospatial information of traffic signal lights, traffic signs, and other road objects and related attributes.

The AV operational database 424 can store raw AV data generated by the sensor systems 404-408 and other components of the AV 402 and/or data received by the AV 402 from remote systems (e.g., the data center 450, the client computing device 470, etc.). In some embodiments, the raw AV data can include HD LIDAR point cloud data, image data, RADAR data, GPS data, and other sensor data that the data center 450 can use for creating or updating AV geospatial data as discussed further below with respect to FIG. 2 and elsewhere in the present disclosure.

The data center 450 can be a private cloud (e.g., an enterprise network, a co-location provider network, etc.), a public cloud (e.g., an Infrastructure as a Service (IaaS) network, a Platform as a Service (PaaS) network, a Software as a Service (SaaS) network, or other Cloud Service Provider (CSP) network), a hybrid cloud, a multi-cloud, and so forth. The data center 450 can include one or more computing devices remote to the local computing device 410 for managing a fleet of AVs and AV-related services. For example, in addition to managing the AV 402, the data center 450 may also support a ridesharing service, a delivery service, a remote/roadside assistance service, street services (e.g., street mapping, street patrol, street cleaning, street metering, parking reservation, etc.), and the like.

The data center 450 can send and receive various signals to and from the AV 402 and client computing device 470. These signals can include sensor data captured by the sensor systems 404-408, roadside assistance requests, software updates, ridesharing pick-up and drop-off instructions, and so forth. In this example, the data center 450 includes a data management platform 452, an Artificial Intelligence/Machine Learning (AI/ML) platform 454, a simulation platform 456, a remote assistance platform 458, a ridesharing platform 460, and map management system platform 462 (e.g., which can include an AV route management system), among other systems.

Data management platform 452 can be a "big data" system capable of receiving and transmitting data at high velocities (e.g., near real-time or real-time), processing a large variety of data, and storing large volumes of data (e.g., terabytes, petabytes, or more of data). The varieties of data can include data having different structure (e.g., structured, semi-structured, unstructured, etc.), data of different types (e.g., sensor data, mechanical system data, ridesharing service, map data, audio, video, etc.), data associated with different types of data stores (e.g., relational databases, key-value stores, document databases, graph databases, column-family databases, data analytic stores, search engine databases, time series databases, object stores, file systems, etc.), data originating from different sources (e.g., AVs, enterprise systems, social networks, etc.), data having different rates of change (e.g., batch, streaming, etc.), or data having other heterogeneous characteristics. The various platforms and systems of the data center 450 can access data stored by the data management platform 452 to provide their respective services.

The AI/ML platform 454 can provide the infrastructure for training and evaluating machine learning algorithms for operating the AV 402, the simulation platform 456, the remote assistance platform 458, the ridesharing platform 460, the map management system platform 462, and other platforms and systems. Using the AI/ML platform 454, data scientists can prepare data sets from the data management platform 452; select, design, and train machine learning models; evaluate, refine, and deploy the models; maintain, monitor, and retrain the models; and so on.

The simulation platform 456 can enable testing and validation of the algorithms, machine learning models, neural networks, and other development efforts for the AV 402, the remote assistance platform 458, the ridesharing platform 460, the map management system platform 462, and other platforms and systems. The simulation platform 456 can replicate a variety of driving environments and/or reproduce real-world scenarios from data captured by the AV 402, including rendering geospatial information and road infrastructure (e.g., streets, lanes, crosswalks, traffic lights, stop signs, etc.) obtained from the map management system platform 462; modeling the behavior of other vehicles, bicycles, pedestrians, and other dynamic elements; simulating inclement weather conditions, different traffic scenarios; and so on.

The remote assistance platform 458 can generate and transmit instructions regarding the operation of the AV 402. For example, in response to an output of the AI/ML platform 454 or other system of the data center 450, the remote assistance platform 458 can prepare instructions for one or more stacks or other components of the AV 402.

The ridesharing platform 460 can interact with a customer of a ridesharing service via a ridesharing application 472 executing on the client computing device 470. The client computing device 470 can be any type of computing system, including a server, desktop computer, laptop, tablet, smartphone, smart wearable device (e.g., smart watch, smart eyeglasses or other Head-Mounted Display (HMD), smart ear pods or other smart in-ear, on-ear, or over-ear device, etc.), gaming system, or other general purpose computing device for accessing the ridesharing application 472. The client computing device 470 can be a customer's mobile computing device or a computing device integrated with the AV 402 (e.g., the local computing device 410). The ridesharing platform 460 can receive requests to be picked up or dropped off from the ridesharing application 472 and dispatch the AV 402 for the trip.

Map management system platform 462 can provide a set of tools for the manipulation and management of geographic and spatial (geospatial) and related attribute data. The data management platform 452 can receive LIDAR point cloud data, image data (e.g., still image, video, etc.), RADAR data, GPS data, and other sensor data (e.g., raw data) from one or more AVs 402, UAVs, satellites, third-party mapping services, and other sources of geospatially referenced data. The raw data can be processed, and map management system platform 462 can render base representations (e.g., tiles (2D), bounding volumes (3D), etc.) of the AV geospatial data to enable users to view, query, label, edit, and otherwise interact with the data. Map management system platform 462 can manage workflows and tasks for operating on the AV geospatial data. Map management system platform 462 can control access to the AV geospatial data, including granting or limiting access to the AV geospatial data based on user-based, role-based, group-based, task-based, and other attribute-based access control mechanisms. Map management system platform 462 can provide version control for the AV geospatial data, such as to track specific changes that (human or machine) map editors have made to the data and to revert changes when necessary. Map management system platform 462 can administer release management of the AV geospatial data, including distributing suitable iterations of the data to different users, computing devices, AVs, and other consumers of HD maps. Map management system platform 462 can provide analytics regarding the AV geospatial data and related data, such as to generate insights relating to the throughput and quality of mapping tasks.

In some embodiments, the map viewing services of map management system platform 462 can be modularized and deployed as part of one or more of the platforms and systems of the data center 450. For example, the AI/ML platform 454 may incorporate the map viewing services for visualizing the effectiveness of various object detection or object classification models, the simulation platform 456 may incorporate the map viewing services for recreating and visualizing certain driving scenarios, the remote assistance platform 458 may incorporate the map viewing services for replaying traffic incidents to facilitate and coordinate aid, the ridesharing platform 460 may incorporate the map viewing services into the client application 472 to enable passengers to view the AV 402 in transit en route to a pick-up or drop-off location, and so on.

Figure 5:
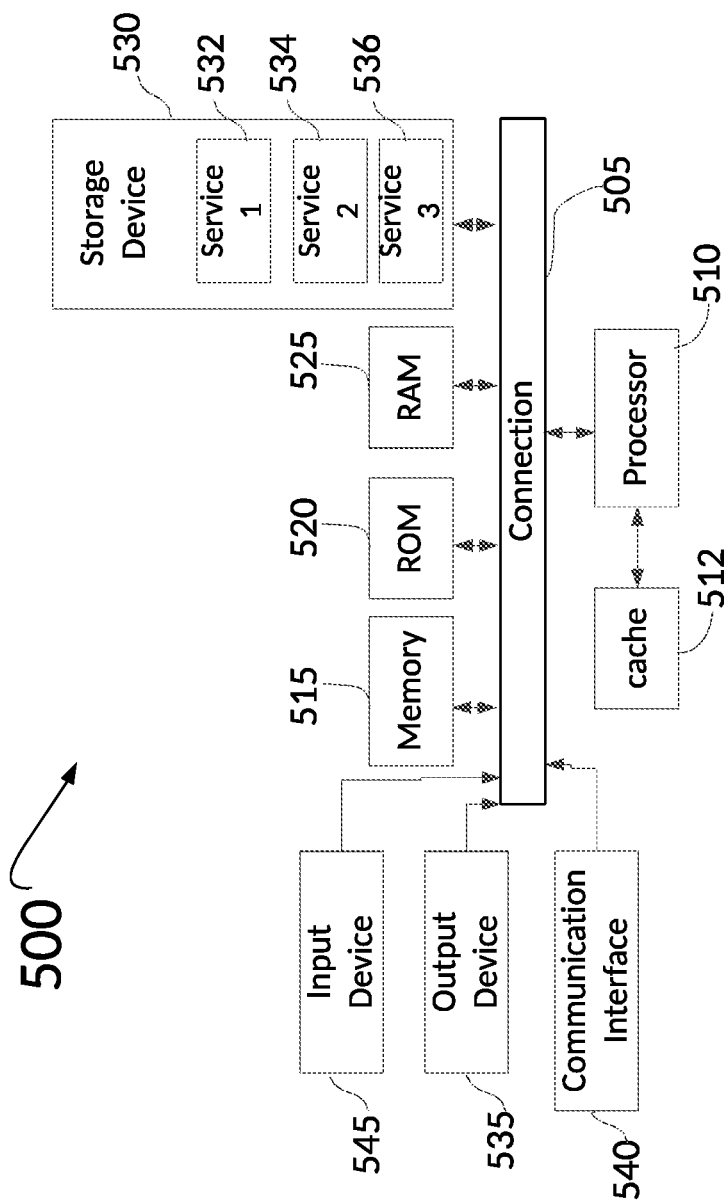
FIG. 5 illustrates an example processor-based system with which some aspects of the subject technology can be implemented.

FIG. 5 illustrates an example processor-based system with which some aspects of the subject technology can be implemented. For example, processor-based system 500 can be any computing device making up internal computing system 510, remote computing system 550, a passenger device executing the rideshare app 570, internal computing device 530, or any component thereof in which the components of the system are in communication with each other using connection 505. Connection 505 can be a physical connection via a bus, or a direct connection into processor 510, such as in a chipset architecture. Connection 505 can also be a virtual connection, networked connection, or logical connection.

In some embodiments, computing system 500 is a distributed system in which the functions described in this disclosure can be distributed within a datacenter, multiple data centers, a peer network, etc. In some embodiments, one or more of the described system components represents many such components each performing some or all of the function for which the component is described. In some embodiments, the components can be physical or virtual devices.

Example system 500 includes at least one processing unit (CPU or processor) 510 and connection 505 that couples various system components including system memory 515, such as read-only memory (ROM) 520 and random access memory (RAM) 525 to processor 510. Computing system 500 can include a cache of high-speed memory 512 connected directly with, in close proximity to, or integrated as part of processor 510.

Processor 510 can include any general purpose processor and a hardware service or software service, such as services 532, 534, and 536 stored in storage device 530, configured to control processor 510 as well as a special-purpose processor where software instructions are incorporated into the actual processor design. Processor 510 may essentially be a completely self-contained computing system, containing multiple cores or processors, a bus, memory controller, cache, etc. A multi-core processor may be symmetric or asymmetric.

To enable user interaction, computing system 500 includes an input device 545, which can represent any number of input mechanisms, such as a microphone for speech, a touch-sensitive screen for gesture or graphical input, keyboard, mouse, motion input, speech, etc. Computing system 500 can also include output device 535, which can be one or more of a number of output mechanisms known to those of skill in the art. In some instances, multimodal systems can enable a user to provide multiple types of input/output to communicate with computing system 500. Computing system 500 can include communications interface 540, which can generally govern and manage the user input and system output. The communication interface may perform or facilitate receipt and/or transmission wired or wireless communications via wired and/or wireless transceivers, including those making use of an audio jack/plug, a microphone jack/plug, a universal serial bus (USB) port/plug, an Apple® Lightning® port/plug, an Ethernet port/plug, a fiber optic port/plug, a proprietary wired port/plug, a BLUETOOTH® wireless signal transfer, a BLUETOOTH® low energy (BLE) wireless signal transfer, an IBEACON® wireless signal transfer, a radio-frequency identification (RFID) wireless signal transfer, near-field communications (NFC) wireless signal transfer, dedicated short range communication (DSRC) wireless signal transfer, 802.11 Wi-Fi wireless signal transfer, wireless local area network (WLAN) signal transfer, Visible Light Communication (VLC), Worldwide Interoperability for Microwave Access (WiMAX), Infrared (IR) communication wireless signal transfer, Public Switched Telephone Network (PSTN) signal transfer, Integrated Services Digital Network (ISDN) signal transfer, 3G/4G/5G/LTE cellular data network wireless signal transfer, ad-hoc network signal transfer, radio wave signal transfer, microwave signal transfer, infrared signal transfer, visible light signal transfer, ultraviolet light signal transfer, wireless signal transfer along the electromagnetic spectrum, or some combination thereof.

Communication interface 540 may also include one or more Global Navigation Satellite System (GNSS) receivers or transceivers that are used to determine a location of the computing system 500 based on receipt of one or more signals from one or more satellites associated with one or more GNSS systems. GNSS systems include, but are not limited to, the US-based Global Positioning System (GPS), the Russia-based Global Navigation Satellite System (GLONASS), the China-based BeiDou Navigation Satellite System (BDS), and the Europe-based Galileo GNSS. There is no restriction on operating on any particular hardware arrangement, and therefore the basic features here may easily be substituted for improved hardware or firmware arrangements as they are developed.

Storage device 530 can be a non-volatile and/or non-transitory and/or computer-readable memory device and can be a hard disk or other types of computer readable media which can store data that are accessible by a computer, such as magnetic cassettes, flash memory cards, solid state memory devices, digital versatile disks, cartridges, a floppy disk, a flexible disk, a hard disk, magnetic tape, a magnetic strip/stripe, any other magnetic storage medium, flash memory, memristor memory, any other solid-state memory, a compact disc read only memory (CD-ROM) optical disc, a rewritable compact disc (CD) optical disc, digital video disk (DVD) optical disc, a blu-ray disc (BDD) optical disc, a holographic optical disk, another optical medium, a secure digital (SD) card, a micro secure digital (microSD) card, a Memory Stick® card, a smartcard chip, a EMV chip, a subscriber identity module (SIM) card, a mini/micro/nano/pico SIM card, another integrated circuit (IC) chip/card, random access memory (RAM), static RAM (SRAM), dynamic RAM (DRAM), read-only memory (ROM), programmable read-only memory (PROM), erasable programmable read-only memory (EPROM), electrically erasable programmable read-only memory (EEPROM), flash EPROM (FLASHEPROM), cache memory (L1/L2/L3/L4/L5/L #), resistive random-access memory (RRAM/ReRAM), phase change memory (PCM), spin transfer torque RAM (STT-RAM), another memory chip or cartridge, and/or a combination thereof.

Storage device 530 can include software services, servers, services, etc., that when the code that defines such software is executed by the processor 510, it causes the system to perform a function. In some embodiments, a hardware service that performs a particular function can include the software component stored in a computer-readable medium in connection with the necessary hardware components, such as processor 510, connection 505, output device 535, etc., to carry out the function.

As understood by those of skill in the art, machine-learning based classification techniques can vary depending on the desired implementation. For example, machine-learning classification schemes can utilize one or more of the following, alone or in combination: hidden Markov models; recurrent neural networks; convolutional neural networks (CNNs); deep learning; Bayesian symbolic methods; general adversarial networks (GANs); support vector machines; image registration methods; applicable rule-based system. Where regression algorithms are used, they may include including but are not limited to: a Stochastic Gradient Descent Regressor, and/or a Passive Aggressive Regressor, etc.

Machine learning classification models can also be based on clustering algorithms (e.g., a Mini-batch K-means clustering algorithm), a recommendation algorithm (e.g., a Miniwise Hashing algorithm, or Euclidean Locality-Sensitive Hashing (LSH) algorithm), and/or an anomaly detection algorithm, such as a Local outlier factor. Additionally, machine-learning models can employ a dimensionality reduction approach, such as, one or more of: a Mini-batch Dictionary Learning algorithm, an Incremental Principal Component Analysis (PCA) algorithm, a Latent Dirichlet Allocation algorithm, and/or a Mini-batch K-means algorithm, etc.

Embodiments within the scope of the present disclosure may also include tangible and/or non-transitory computer-readable storage media or devices for carrying or having computer-executable instructions or data structures stored thereon. Such tangible computer-readable storage devices can be any available device that can be accessed by a general purpose or special purpose computer, including the functional design of any special purpose processor as described above. By way of example, and not limitation, such tangible computer-readable devices can include RAM, ROM, EEPROM, CD-ROM or other optical disk storage, magnetic disk storage or other magnetic storage devices, or any other device which can be used to carry or store desired program code in the form of computer-executable instructions, data structures, or processor chip design. When information or instructions are provided via a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable storage devices.

Computer-executable instructions include, for example, instructions and data which cause a general-purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform tasks or implement abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Other embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

The various embodiments described above are provided by way of illustration only and should not be construed to limit the scope of the disclosure. For example, the principles herein apply equally to optimization as well as general improvements. Various modifications and changes may be made to the principles described herein without following the example embodiments and applications illustrated and described herein, and without departing from the spirit and scope of the disclosure. Claim language reciting "at least one of" a set indicates that one member of the set or multiple members of the set satisfy the claim.

What is claimed is:

1. An autonomous vehicle (AV), comprising:
   one or more processors; and
   a computer-readable medium coupled to the one or more processors, wherein the computer-readable medium comprises instructions that are configured to cause the one or more processors to:
   collect sensor-data corresponding with one or more AV passengers, wherein the sensor-data is based on a microphone located on the exterior of the AV;
   determine a likelihood that at least one of AV passengers is suffering from a physical illness before the one or more AV passengers enter the AV;
   transmit a wellness notification to a fleet management system if the likelihood exceeds a predetermined threshold; and
   receive a response from the fleet management system, based on the wellness notification, wherein the response is configured to cause the AV to be decommissioned to perform cleaning procedures to disinfect the AV.

2. The AV of claim 1, wherein the computer-readable medium further comprises instructions that are configured to cause the one or more processors to:
   receive a response from the fleet management system, based on the wellness notification, wherein the response is configured to cause the AV to be temporarily suspended from service.

3. The AV of claim 1, wherein the likelihood that at least one of the one or more AV passengers is suffering from a physical illness is based on a fever detected for at least one of the one or more AV passengers.

4. The AV of claim 1, wherein the likelihood that at least one of the one or more AV passengers is suffering from a physical illness is based on a respiratory irregularity detected for at least one of the one or more AV passengers.

5. The AV of claim 1, wherein the sensor-data comprises data collected from a thermal sensor, a microphone, or a combination thereof.

6. The AV of claim 5, wherein the thermal sensor comprises a thermal camera, a thermometer, or a combination thereof.

7. The AV of claim 1, wherein the sensor-data comprises data collected from within a cabin of the AV.

8. A computer-implemented method for assessing a passenger health state, comprising:
   collecting sensor-data corresponding with one or more AV passengers, wherein the sensor-data is based on a microphone located on the exterior of the AV;
   determining a likelihood that at least one of the AV passengers is suffering from a physical illness before the one or more AV passengers enter the AV;
   transmitting a wellness notification to a fleet management system if the likelihood exceeds a predetermined threshold; and
   receiving a response from the fleet management system, based on the wellness notification, wherein the response is configured to cause the AV to be decommissioned to perform cleaning procedures to disinfect the AV.

9. The computer-implemented method of claim 8, further comprising:
   receiving a response from the fleet management system, based on the wellness notification, wherein the response is configured to cause the AV to be temporarily suspended from service.

10. The computer-implemented method of claim 8, wherein the likelihood that at least one of the one or more AV passengers is suffering from a physical illness is based on a fever detected for at least one of the one or more AV passengers.

11. The computer-implemented method of claim 8, wherein the likelihood that at least one of the one or more AV passengers is suffering from a physical illness is based on a respiratory irregularity detected for at least one of the one or more AV passengers.

12. The computer-implemented method of claim 8, wherein the sensor-data comprises data collected from a thermal sensor, a microphone, or a combination thereof.

13. The computer-implemented method of claim 12, wherein the thermal sensor comprises a thermal camera, a thermometer, or a combination thereof.

14. The computer-implemented method of claim 8, wherein the sensor-data comprises data collected from within a cabin of the AV.

15. A non-transitory computer-readable storage medium comprising instructions stored therein, which when executed by one or more processors, cause the processors to perform operations comprising:
    collecting sensor-data corresponding with one or more AV passengers, wherein the sensor-data is based on a microphone located on the exterior of the AV;
    determining a likelihood that at least one of the AV passengers is suffering from a physical illness before the one or more AV passengers enter the AV;

transmitting a wellness notification to a fleet management system if the likelihood exceeds a predetermined threshold; and receiving a response from the fleet management system, based on the wellness notification, wherein the response is configured to cause the AV to be decommissioned to perform cleaning procedures to disinfect the AV.

16. The non-transitory computer-readable storage medium of claim 15, wherein the processors are further configured to perform operations comprising:

receiving a response from the fleet management system, based on the wellness notification, wherein the response is configured to cause the AV to be temporarily suspended from service.

17. The non-transitory computer-readable storage medium of claim 15, wherein the likelihood that at least one of the one or more AV passengers is suffering from a physical illness is based on a fever detected for at least one of the one or more AV passengers.

18. The non-transitory computer-readable storage medium of claim 15, wherein the likelihood that at least one of the one or more AV passengers is suffering from a physical illness is based on a respiratory irregularity detected for at least one of the one or more AV passengers.

19. The non-transitory computer-readable storage medium of claim 15, wherein the sensor-data comprises data collected from a thermal sensor, a microphone, or a combination thereof.

20. The non-transitory computer-readable storage medium of claim 19, wherein the thermal sensor comprises a thermal camera, a thermometer, or a combination thereof.

* * * * *